US010186994B2

(12) United States Patent
Neyer et al.

(10) Patent No.: US 10,186,994 B2
(45) Date of Patent: Jan. 22, 2019

(54) SHAVER MOTOR SPEED CONTROL

(71) Applicant: Braun GmbH, Kronberg (DE)

(72) Inventors: Christian Neyer, Eschborn (DE); Holger Hild, Idstein (DE); Felix Koenig, Darmstadt (DE); Gerd Laschinski, Oberursel (DE)

(73) Assignee: Bruan GMBH, Kronberg (DE)

( * ) Notice: Subject to any disclaimer, the term of this patent is extended or adjusted under 35 U.S.C. 154(b) by 0 days.

(21) Appl. No.: 15/817,578

(22) Filed: Nov. 20, 2017

(65) Prior Publication Data

US 2018/0145618 A1 May 24, 2018

(30) Foreign Application Priority Data

Nov. 23, 2016 (EP) .................................... 16200288
Nov. 14, 2017 (EP) .................................... 17201508

(51) Int. Cl.

| | |
|---|---|
| ***H02P 23/00*** | (2016.01) |
| ***H02P 25/00*** | (2006.01) |
| ***H02P 27/00*** | (2006.01) |
| ***H02P 7/06*** | (2006.01) |
| ***B26B 19/38*** | (2006.01) |
| ***A61B 17/50*** | (2006.01) |
| ***B26B 19/28*** | (2006.01) |
| ***H02P 29/00*** | (2016.01) |
| ***H02P 7/28*** | (2016.01) |
| ***H02P 7/29*** | (2016.01) |
| *A45D 26/00* | (2006.01) |
| *A61B 17/00* | (2006.01) |

(52) U.S. Cl.

CPC ................ *H02P 7/06* (2013.01); *A45D 26/00* (2013.01); *A61B 17/50* (2013.01); *B26B 19/28* (2013.01); *B26B 19/388* (2013.01); *B26B 19/3813* (2013.01); *B26B 19/3873* (2013.01); *H02P 7/2805* (2013.01); *H02P 7/29* (2013.01); *H02P 29/0016* (2013.01); *A45D 2026/0095* (2013.01); *A61B 2017/00752* (2013.01)

(58) Field of Classification Search

CPC ............ H02P 7/06; A45D 26/00; A61B 17/50
USPC .......................................................... 318/799
See application file for complete search history.

(56) References Cited

U.S. PATENT DOCUMENTS

| | | | | |
|---|---|---|---|---|
| 5,367,599 A | 11/1994 | Okada | | |
| 2010/0263895 A1* | 10/2010 | Bosch | H02M 1/44 | 173/217 |
| 2011/0015788 A1* | 1/2011 | Celik | H02P 6/14 | 700/275 |
| 2015/0288312 A1 | 10/2015 | Ibuki et al. | | |
| 2015/0365030 A1* | 12/2015 | Tsai | H02P 7/29 | 318/504 |

(Continued)

FOREIGN PATENT DOCUMENTS

| | | |
|---|---|---|
| JP | H11235069 | 8/1999 |

OTHER PUBLICATIONS

European search report dated Jun. 12, 2017.

*Primary Examiner* — Erick Glass
(74) *Attorney, Agent, or Firm* — Ronald T. Sia; Kevin C. Johnson

(57) ABSTRACT

The invention is related to a drive control for driving a dc motor of an electrical household appliance, in particular a hair cutting device such as an electric razor, shaver or epilator, at constant rotational speed.

16 Claims, 3 Drawing Sheets

32 1 2 M $R_m$ $U_m$ $U_{emf}$ U I PWM 40 $U_{DSon}$ 10 $U_s$ $R_s$ 31 30 33 34 21 20

(56) References Cited

U.S. PATENT DOCUMENTS

2016/0000202 A1* 1/2016 Ohba .................... B26B 19/282
606/133

* cited by examiner

SHAVER MOTOR SPEED CONTROL

FIELD OF THE INVENTION

A drive control for driving a dc motor of an electrical household appliance. The household electrical appliance can be in particular a hair removing device such as a razor, shaver, epilator or the like. The drive control comprises a detection means for determining a parameter indicative of the actual rotational speed of the dc motor and a closed loop control for adjusting a supply voltage to the dc motor based on a control deviation between a target value and the actual value of the parameter indicative of the rotational speed of the dc motor.

BACKGROUND OF THE INVENTION

The rotational speed of a dc motor decreases when the mechanical load of the motor increases. At least, this is true when no countermeasures are taken. In the case of a shaver with a rotating motor, the decrease in motor speed translates in reduced shaving performance In the GB 2 435 413 A, a drive circuit for a hair clipper is described. The hair clipper comprises an electric motor and a control circuit for operating the motor at a constant speed regardless of load condition. Constant clipper speed is achieved by increasing the voltage in response to a sensed increase in load current, caused by increased work required of the clippers due to eg. lack of lubrication. The control circuit comprises detector means for sensing the supply voltage to the clipper and the clipper current, processing means for generating an error signal indicative of a change in supply voltage needed to maintain a constant motor speed and a pulse width modulation (PWM) module responsive to the error signal for adjusting the supply voltage to the clipper to drive the motor at said constant speed.

Such load compensation electronics have been developed to compensate the speed change of a shaver dc motor under load. However, it was observed that the motor did not run constantly and smoothly any more. This could be measured under constant load. The effect was in particular present when the dc motor was running without load, i.e. without really shaving in that moment.

SUMMARY OF THE INVENTION

It is accordingly an object of the invention to provide a drive control for a dc motor of an electrical household appliance providing constant motor speed in cases with varying load and with constant (not varying and in particular no) load.

The proposed drive control according to the invention comprises:

- a detection means for determining a parameter indicative of the actual rotational speed of the dc motor and
- a closed loop control for adjusting a supply voltage to the dc motor based on a control deviation between a target value and the actual value of the parameter indicative of the rotational speed of the dc motor.

The supply voltage is adjusted such by a controller of the closed loop control that the control deviation is eliminated or reduced. This is the known basic principle of closed loop controls. The term "adjusting the supply voltage" comprises for the present disclosure a control of parameters of a Pulse Width Modulation (PWM), in particular the duty cycle. For the modulation of the PWM duty cycle, the dc motor switches on and off in very short time intervals. Very short time intervals meant that the switching on and off of the dc motor is not recognized by the user during use of electrical household appliance, e.g. the shaver. The modulation of the PWM duty cycle leads to an adjustment of the mean supply voltage to the dc motor and, therewith, to an adjustment of the motor rotational speed.

According to the invention, the closed loop control further has:

- a fast control and a slow control for adjusting the supply voltage with the fast control providing a faster correction of the control deviation than the slow control,
- a processor means (also denoted "processor" in the following) for determining a switching criterion for switching between the fast control and the slow control, wherein the close loop control is adapted for switching between the fast control and the slow control based on the switching criterion.

The faster correction of the fast control results in a shorter control response time compared to the slow control.

Another aspect of the invention is related to an electric hair and/or skin treating device having a main body with a dc-motor for driving a treating tool, a power source and a drive control as described before.

Further features of the proposal according to the invention are described in the dependent claims and the following detailed description of the invention.

DETAILED DESCRIPTION OF THE INVENTION

Figure 1:
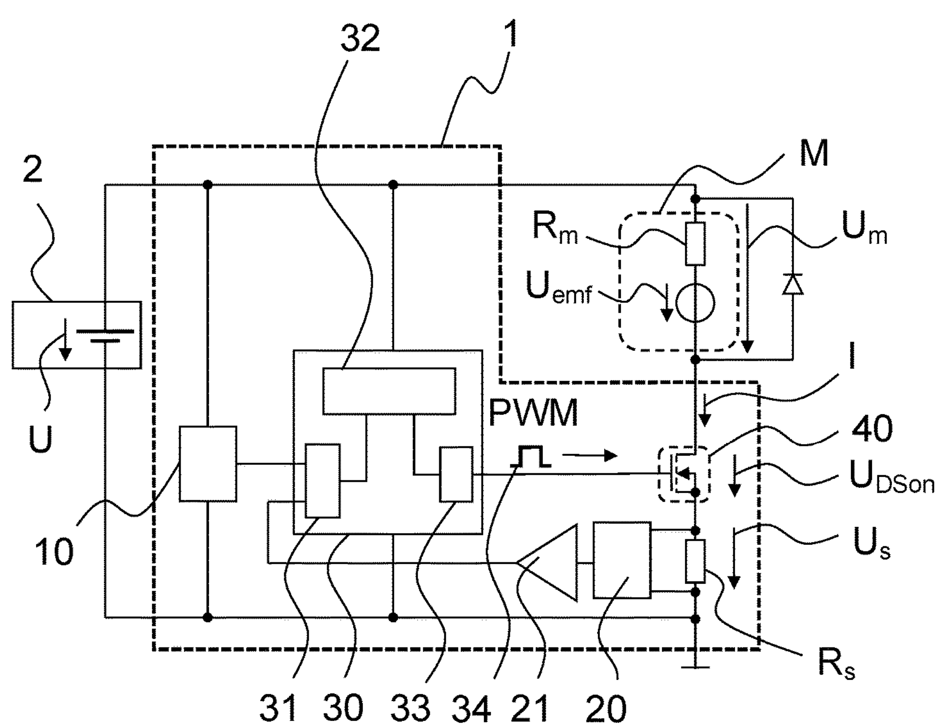
FIG. 1 schematically shows a drive control according to an embodiment of the invention which drives a dc motor.

Before describing advantageous embodiments of the invention related to the FIGS. 1 to 4, different aspects of the invention are described more in detail. These aspects disclose further features, advantages and possibilities of use of the present invention that might be combined in any useful combination. All features described and/or shown in the drawings are subject matter of the invention, irrespective of the grouping of the features in the claims and/or their back references.

The proposed drive control is adapted for driving a dc motor of an electrical household appliance, in particular a hair cutting device such as an electric shaver or epilator, at constant rotational speed. Either the fast control or the slow control is applied when the motor is running "A switching criterion for switching between the fast control and the slow control" means that there is at least one switching criterion for switching from the slow control to the fast control and/or from the fast control to the slow control.

Any switching criterion for switching from the slow control to the fast control is denoted as an "upshift switching criterion" and any switching criterion for switching from the fast control to the slow control is denoted as a "downshift switching criterion". A switching criterion for both directions is denoted as a "bidirectional switching criterion". The term "switching criterion" is used as a general term for all these cases.

The drive control may comprise arbitrary combinations of the different kinds of switching criteria. Several switching criteria of the same kind may be provided. According to the invention, at least one switching criterion exhibiting upshift (i.e. an upshift switching criterion or a bidirectional switching criterion) and at least one switching criterion exhibiting downshift (i.e. a downshift switching criterion or a bidirectional switching criterion) are provided.

In an embodiment of the proposal, the switching criterion is derived from the parameter indicative of the actual rotational speed. By this, the type of control which is more adequate for the actual rotational speed and/or a change of the actual rotational speed can be chosen. As noted above, without countermeasures, the rotational speed of the dc motor decreases when a mechanical load increases. Consequently, with this embodiment, the switching between the slow control and the fast control can be adjusted to the actual mechanical load and/or changes of the mechanical load.

For example, if the actual rotational speed is within a desired range and does not change, or changes with a change rate less than a maximum change rate, the drive control may be switched to the slow control to avoid unnecessary, quick fluctuations of the rotational speed due to the shorter response time of the fast control. If the slow control is active but a load on the dc motor increases quickly, the slow control's control response time may be too long to adjust the voltage supply of the dc motor fast enough to keep the rotational speed within a desired range. Hence, as a countermeasure, it can be switched to the fast control with shorter control response time.

There may be more than one parameter indicative of the rotational speed of the dc motor and several corresponding control deviations. Each switching criterion may consider one or more of the parameters indicative of the rotational speed of the dc motor. In the following, the term "indicative parameter" is used as short version of the term "parameter indicative of the rotational speed of the dc motor".

The actual rotational speed of the dc motor may be derivable from the (at least one) indicative parameter. This means that the actual rotational speed and/or its absolute or relative difference from a target rotational speed can be—at least approximately—determined when considering an actual value of the indicative parameter. Therefore, the control deviation, the target value and the actual value of the indicative parameter may be correlated to a corresponding deviation, target value and actual value of the rotational speed of the dc motor. If there are several indicative parameters, the actual rotational speed is derivable from one, several or at least all of the indicative parameters.

In another aspect, the processor is adapted to derive the actual rotational speed from the actual value of the indicative parameter. Hence, the rotational speed is provided without directly measuring it.

In yet another embodiment, the switching criterion comprises or is derived from a threshold value for the control deviation. The value of the control deviation may be an absolute or a relative value. Implementing a switching criterion with a threshold value for the control deviation is an easy way for considering the actual rotational speed of the dc motor for switching. It is not necessary to measure the actual rotational speed directly. Therefore, the drive control is cheaper and more reliable.

For example, the switching criterion may comprise a negative threshold. Accordingly, the actual value of the indicative parameter has to be smaller than the target value by a certain amount or relation (relative value) to fulfill the criterion. Likewise, the switching criterion may comprise a positive threshold or both a negative threshold and a positive threshold. In the latter case, of course only one of these thresholds has to be exceeded to fulfill the switching criterion. If the negative threshold and the positive threshold have the same absolute value, this is called "absolute value threshold".

In another embodiment, there is at least one upshift switching criterion and at least one downshift switching criterion which is different from the at least one upshift switching criterion. This means that different switching criteria are applied for switching from the slow control to the fast control and vice versa (hysteresis effect). Thus, ongoing switching forth and back which could happen if the actual value of the indicative parameter would fluctuate around a threshold of a bidirectional switching criterion is avoided.

In yet another embodiment, the switching criterion may comprise a time threshold. Preferably, the time threshold may require that the control deviation has to fulfill another requirement (for example the control deviation being in a particular range or above/below a threshold value) for a certain period of time. Additionally or alternatively, most preferably when the fast control is used, the time threshold may require that a current type of control has been used for the certain period of time. By implementing the time threshold, hectic switching between the fast control and the slow control can be suppressed.

According to another aspect of the proposal, the at least one upshift switching criterion comprises an upshift absolute threshold for the control deviation and the at least one downshift switching criterion comprises a downshift absolute threshold for the control deviation and a downshift time threshold, wherein the downshift absolute threshold is equal or less than the upshift absolute threshold. When the slow control is active, as soon as an absolute value of the control deviation exceeds the absolute upshift value, switching to the fast control takes place. Accordingly, supposed the fast control is used and the absolute value of the control deviation is less than downshift absolute threshold for a time period equal to (or longer than) the time threshold, the downshift criterion is fulfilled and switching to the slow control takes place. With these criteria, it can be ensured that it is only switched back to the slow control after a severe load change has ended.

In another aspect, an upshift threshold of a switching criterion for exhibiting upshift (i.e. an upshift switching criterion or a bidirectional switching criterion) and a downshift threshold of another switching criterion for exhibiting downshift (i.e. a downshift switching criterion or a bidirectional switching criterion) are different from each other. As described above, unwanted repeated switching due to fluctuations can be avoided by these different criteria.

According to sill another preferred embodiment of the proposal, the fast control is able to deliver a larger impact on the rotational speed of the dc motor per time unit than the slow control. Thus, the fast control can quickly compensate for fast and large changes of the load of the dc motor.

According to another aspect, a control output of the fast control might have a term proportional, integrative and/or derivative to the control deviation. Preferably, the fast control can be a PID-controller. Thus, the response of the fast control is a direct function of the control deviation (also called error value). The amount of the response depends on the amount the control deviation. As a consequence, the response reacts very fast on a control deviation and tries to eliminate it fast. Preferably, the PID-Controller is a software-implemented PID-Controller.

In a preferred embodiment of the proposal, the slow control might also have a proportional term, an integrative term and/or a derivative term, the coefficients of these terms of the slow control being defined thus that the amount of controller put is smaller than the amount of the fast control.

In yet another embodiment, a fast control algorithm is provided and the processor is adapted to execute the fast control algorithm to exhibit the fast control. Alternatively or additionally, a slow control algorithm may be provided, wherein the processor is adapted to execute the slow control algorithm for exhibiting the slow control. The closed loop control may further comprise a memory. The memory may be connected to the processor or be a part of the processor.

In another aspect, the drive control comprises a microcontroller including the processor which is adapted to exhibit the fast control and the slow control and the switching between them. Preferably, the microcontroller further comprises an analog-to-digital-converter and/or the memory.

According to still another aspect, the change rate of the rotational speed per time unit caused by the slow control might be limited by a predetermined maximum change rate. Thus it is avoided that the slow control is prone to cause excessive fluctuations of the rotational speed of the dc motor. This ensures a uniform, smooth and pleasant run of the dc motor when the slow control is active. Preferably, the predetermined maximum change rate limits the absolute value of the change rate of the rotational speed per time unit. This refers to both, acceleration and deceleration.

In a preferred embodiment, the control output of the slow control provides discrete limited steps. By choosing a switching criterion that switches between the fast control and the slow control on basis of the amount of the control deviation, it is possible to adjust the discrete limited steps and the proportional, integrative and/or derivative term of the fast control such that the control output of the slow control has a smaller amount than that of the fast control. For example, the fast control might be switched on only for an amount of the control deviation leading to a higher control output than the discrete limited steps.

According to another aspect, the control output of the slow control only adopts any state for changing the rotational speed of the dc motor when the absolute value of the control deviation exceeds a minimum absolute value. This results in avoiding unnecessary corrections of small fluctuations of the rotational speed around the target speed.

Further, the control output of the slow control may only depend on the control deviation exceeding a minimum absolute value and on its sign. Therefore, the control output of the slow control can only adopt three different stages, for example only +1 (acceleration), 0 (no change of rotational speed), or −1 (deceleration).

Alternatively, the control output of the slow control may adopt more than three discrete limited stages depending on the value of the control deviation. For example, the control output may adopt the values +2, +1, 0, −1, −2. For instance, the control output +2 corresponds to an acceleration of the rotational speed of $+2/s^2$, the control output −1 may correspond to a deceleration of $1/s^2$, and the control output 0 may correspond to no change of the rotational speed, and so on.

In still another aspect, a slow loop frequency of the slow control is less than a fast loop frequency of the fast control. This is an easy way to increase the control response time of the slow control and to ensure a uniform, smooth and pleasant run of the dc motor when the slow control is used. The slow loop frequency may also delimit the maximum achievable change rate of the rotational speed per time unit that can be caused by the slow control.

Alternatively, the same loop frequency is used for both the slow control and the fast control. This simplifies the closed loop control.

According to a preferred embodiment of the proposal, the closed loop control comprises a pulse width modulation (PWM) module for adjusting the supply voltage to the dc motor. Preferably, the PWM module controls a transistor which regulates a motor current of the dc motor. This is a cost-efficient and reliable way for adjusting the supply voltage of the motor.

In another aspect, the parameter indicative of the actual rotational speed of the dc motor is the induced motor voltage and/or the rotational speed (n) defined as rotations per time. The induced motor voltage is induced be the rotation of the motor and is proportional to the rotational speed of the motor. It can be measured easily and reliably with common means and allows deriving the rotational speed. Measuring only the induced voltage keeps the drive control—especially its detection means of the drive control—simple and cheap and further allows an indirect measurement of the rotational speed. The dimension of the rotational speed might be 1/s.

In still another aspect, the detection means for determining a parameter indicative of the actual rotational speed of the dc motor comprise means for determining the dc voltage of the power source of the electrical appliance and/or for determining the motor current. The dc voltage of the power source, e.g. a rechargeable/secondary battery, and the motor current may be used on basis of a model of the dc motor to calculate the rotational speed. The advantages have already been noted.

The present invention is also directed to an electric hair and/or skin treating device (such as a shaver or epilator) as electrical household appliance having a main body with a dc-motor for driving a treating tool, a power source (such as rechargeable/secondary battery) and a drive control described above.

According to a preferred embodiment of the invention, the treating tool comprises a modular element detachable and re-attachable to the electric hair and/or skin treating device by coupling the treating tool to a drive mechanism of the electrical hair and/or skin treating device driven by the dc-motor. Therefore, the electric hair and/or skin treating device can be used with different modular elements and its area of application is enhanced. Furthermore, the modular element can be replaced if it is broken or if an improved element is available.

According to another embodiment, the modular element comprises a brush, a beard trimmer, a body groomer and/or a shaver. Thus, the electric hair and/or skin treating device can be applied for the different respective household appliance(s) and constitute a multi-purpose device.

In another aspect, the drive control is adapted to control the rotational speed irrespective of the load to an adjustable target rotational speed. Preferably, the switching criterion is different for at least two modular elements. Additionally or alternatively, one or more parameters of the closed control loop, for example the target rotational speed, a threshold, the low loop frequency and/or the fast loop frequency may be different for at least two different modular elements.

Figure 4:
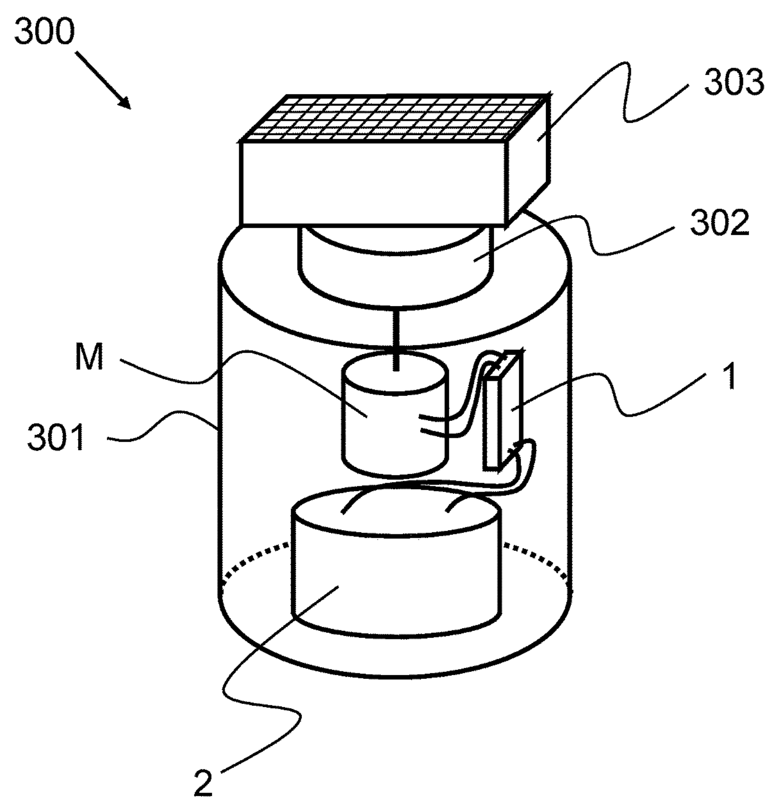
FIG. 4 schematically shows an electric hair and skin treating device using the drive control of FIG. 1.

In FIG. 1, an embodiment of a drive control 1 according to the proposal drives a dc motor M of an electrical hair and skin treating device 300 illustrated in FIG. 4. A power source 2 provides the drive control 1 and the motor M with a dc voltage U. The power source 2 is a rechargeable battery. The motor M is switched on and off and operated by means of a transistor 40 with a resistance $R_{DSon}$. The transistor 40 is operated and controlled by the microcontroller 30. More precisely, the transistor 40 is operated by a PWM signal 34 of a variable duty cycle p (not shown) which is sent from an PWM module 33 of the microcontroller 30.

The motor current I driving the motor M passes a shunt resistor $R_S$ and generates a voltage drop $U_S$. This voltage $U_S$ is filtered by a low pass filter 20. The resulting signal is amplified by an amplifier 21 and measured an analog-to-digital-converter 31 of the microcontroller 30. Therefore, the shunt resistor $R_S$, the low pass filter 20, the amplifier 21 and the analog-to digital-converter 31 constitute a detection means for determining a filtered motor current $\bar{I}$.

In addition, the voltage U is filtered by another low pass filter 10 and measured via the analog-to-digital-converter 31 of the microcontroller 30. Therefore, the low pass filter 10 and the analog-to-digital-converter 31 constitute a detection means for determining a filtered voltage $\bar{U}$ of the power source 2.

A rotational speed n of the dc motor n is calculated on basis of the filtered voltage $\bar{U}$, the filtered motor current $\bar{I}$ and the PWM duty cycle p. This is explained in the following:

The dc motor M generates an internal voltage $U_{emf}$ [V] which can be calculated as $$U_{emf}=2\pi\cdot k_e\cdot n$$

when rotating with the rotational speed n [1/s]. A motor constant $k_e$ [Vs]=[Nm/A] is used for the calculation. Due to PWM with duty cycle p, a voltage drop $U_{DSon}$ on the transistor with resistance $R_{DSon}$, and the shunt resistor ($R_S$), a motor voltage $U_m$ of $$U_m=\bar{U}\cdot p-(R_{DSon}+R_S)\cdot\bar{I}$$

is actually applied to the motor M. The induced voltage $U_{emf}$ can be calculated as $$U_{emf}=U_m-R_m-\bar{I}$$

with a motor resistance $R_m$. Therefore, the rotational speed n can be calculated as $$2\pi\cdot k_e\cdot n=\bar{U}\cdot p-(R_{DSon}+R_S)\cdot\bar{I}-R_m\cdot\bar{I}$$

$$n(\bar{U},\bar{I},p)=\frac{1}{2\pi\cdot k_e}(\bar{U}\cdot p-(R_{DSon}+R_S+R_m)\cdot\bar{I}).$$

Alternatively, the motor speed can be taken from a look up table.

It is evident that the measured filtered motor current $\bar{I}$ is indicative of the rotational speed n of the dc motor M. In principle, the voltage U (or the filtered voltage $\bar{U}$) of the power source 2 does not have to be measured, as long as it is known and sufficiently constant. However, measuring the filtered voltage $\bar{U}$ has the advantage that the drive control can consider if the voltage of the voltage source 2 drops, for example, when the rechargeable battery is low.

A processor 32 of the microcontroller 30 is connected to the analog-to-digital-converter 31 and processes the measured current $\bar{I}$ and the measured voltage $\bar{U}$. Furthermore, the processor 32 is adapted to execute algorithms for exhibiting a fast control and a slow control. The microcontroller comprises a memory (not shown) connected to the processor or being part of the processor, in which these algorithms are stored. The motor constant $k_e$ is stored in the memory as well.

The processor 32 is adapted to calculate the induced voltage $U_{emf}$ on the basis of the current $\bar{I}$ and the voltage $\bar{U}$. It is further adapted to calculate a control deviation D between the induced voltage $U_{emf}$ and a nominal value (or target value) of the induced voltage $U_{emf,0}$ which corresponds to a target value $n_0$ of the rotational speed n:

$$D=U_{emf}-U_{emf,0}.$$

The respective target current $U_{emf,0}$ is stored in the memory.

The processor 32 further determines switching criteria for switching between the fast control and the slow control. If a respective criterion is fulfilled, the drive control 1 switches from the fast control to the slow control or vice versa.

Either the slow control or the fast control (whichever is used at the moment) generates a control output, wherein the control deviation D is considered.

Furthermore, the processor 32 is connected to the PWM module 33 of the microcontroller 30. The PWM module 33 generates the PWM signal 34 with duty cycle p depending on the control output to operate the transistor 40. The actual motor voltage $U_m$ is adjusted by changing the duty cycle p considering the control Deviation D.

As the current $\bar{I}$ and the voltage $\bar{U}$ are measured again, a closed loop control is established.

As an alternative, the processor 32 calculates the actual rotational speed n and the control deviation D is calculated as a difference between a target value $n_0$ for the rotational speed and the actual rotational speed n. The respective target value $n_0$ is stored in the memory.

Figure 2:
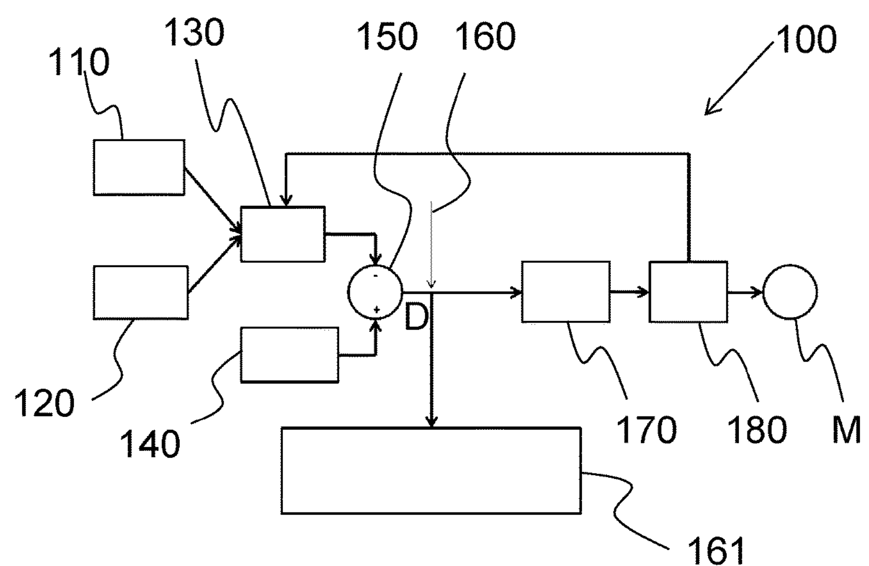
FIG. 2 shows a flow chart schematically illustrating the closed loop when a fast control of the drive control of FIG. 1 is used.

The closed loop control 100 realized in the microprocessor 30 using the fast control is further explained with regard to FIG. 2. In step 110, the battery voltage $\bar{U}$ is measured. Furthermore, the motor current $\bar{I}$ is measured in step 120. These measurement results and the actual duty cycle p are used as input for a calculation of the induced internal voltage $U_{emf}$ in step 130.

A target value of the nominal value $U_{emf,0}$ is provided in step 140. In step 150, the calculated induced voltage $U_{emf}$ and the nominal value $U_{emf,0}$ of the induced voltage are compared. More precisely, the calculated induced voltage $U_{emf}$ is subtracted from nominal value $U_{emf,0}$ to obtain the control deviation D. Then, a "downshift" switching criterion for switching from the fast control to the slow control is determined in step 160. The downshift switching criterion consists of the following two requirements:

a) The absolute value of the control deviation D is less than a downshift absolute threshold $W_{D,d}$ which corresponds to a deviation of the actual rotational speed n of the motor from its target value $n_0$ of e.g. 3 turns per second:

$$|D|<|W_{D,d}|$$

A reasonable range for this downshift absolute threshold $W_{D,d}$ might be in the range between 1 and 10 turns per second.

b) The requirement a) has been fulfilled continuously for at least 1.5 seconds (time threshold).

A reasonable time range might be 0.5 to 5 seconds.

Figure 3:
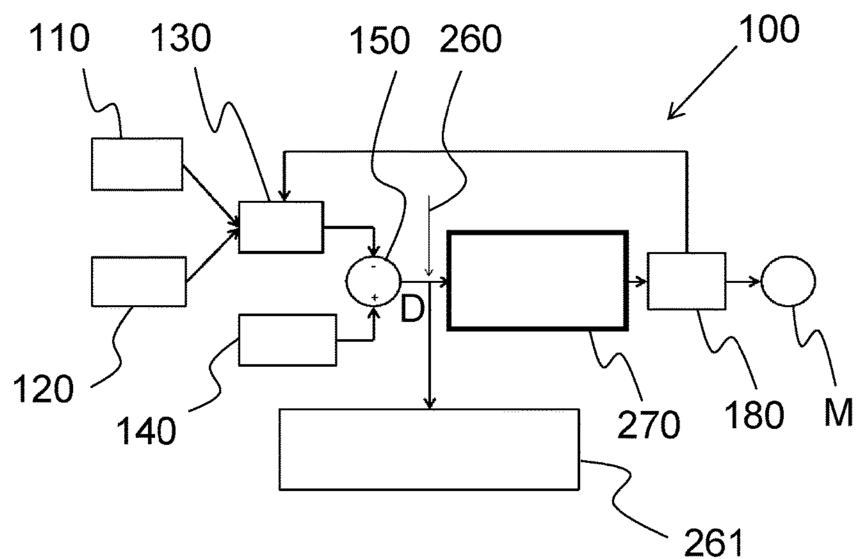
FIG. 3 shows a flow chart schematically illustrating the closed loop when a slow control of the drive control of FIG. 1 is used.

If both requirements, and hence the downshift switching criterion, are fulfilled, switching to the slow control takes place in step 161, the slow control continuing then with step 270 (FIG. 3). If not, the fast control is used further and proceeds to step 170.

In general, different downshift absolute thresholds and different time thresholds are used for different modular elements 303 as shown in FIG. 4.

In the latter case, in step 170 a software implemented PID controller generates a control output on the basis of the control deviation D. The control output is used as input for a PWM generation in step 180. As a consequence, the duty cycle p is corrected on the basis of the control deviation D, if necessary. The amount of the response of the PID controller (i.e. the correction of the duty cycle p) depends linearly on the amount of the control deviation D. By this, even larger control deviations D can be corrected by the closed control loop using the fast control. The PWM signal is used for operating the dc motor M. Finally, the fast loop starts again.

The closed loop control 100 using the slow control is further explained with regard to FIG. 3. The steps having the same reference signs as in FIG. 2 correspond to those of the fast control and are not explained again. In the main, the slow control differs from the fast control in the steps 260, 261 and 270.

In step 270, similar as in step 170 of the fast control, a control output is generated on the basis of the control deviation D and used as input for the PWM generation in step 180. However, the increment and decrement of the PWM value are limited such that the slow control causes an acceleration of the motor M of $+1/s^2$ at the maximum or $-1/s^2$ at the minimum in one cycle of the loop.

Moreover, the duty cycle p is not adapted if the absolute value of the control deviation D is less than a correction threshold $W_C$. The correction threshold $W_C$ corresponds to a deviation of e.g. 0.5 turns per second of the rotational speed n from its target value $n_0$. A reasonable range for the correction threshold $W_C$ might be in the range of 0 to 3 turns per second. Consequently, slight fluctuations of the rotational speed n are permitted in the slow control to avoid unnecessary corrections and unwanted back coupling which would cause repeated fluctuation of the rotational speed n and thus unpleasant vibrations and sounds of the motor M. In case of a correction threshold $W_C$ having the value zero, the PWM-value is changed in every cycle. Since this happens very quickly, it may probably not be audible.

Apart from that, a loop frequency of the slow control might be smaller than or equal to a loop frequency of the fast control. For the slow control, an exemplary loop frequency suited e.g. for a shaver or epilator might be ranged between 50 Hz and 100 kHz. One example might be a loop frequency of about 2 kHz and a limitation of the maximum rate for changing the PWM-value to about 122 Hz.

For the fast control, an exemplary loop frequency suited e.g. for a shaver or epilator might be ranged between 100 Hz and 200 kHz. One example might be a loop frequency of about 2 kHz and a limitation of the maximum rate for changing the PWM-value to about the same value of 2 kHz.

Summed up, a control response time of the slow control might be longer than a control response time of the fast control.

An "upshift" switching criterion for switching from the slow control to the fast control is determined in step 260. The upshift switching criterion is fulfilled if the absolute value of the control deviation D is larger than an upshift absolute threshold $W_{D,u}$ which corresponds to a deviation of 3 turns per second of the rotational speed n from its target value $n_0$. A suited range might be from 1 to 10 turns per second for an household appliance, such as a shaver or epilator. It should be noted that the upshift absolute threshold $W_{D,u}$ is the same as the downshift absolute threshold $W_{D,d}$ in this embodiment. However, they may differ in other embodiments. If the absolute value of the control deviation D exceeds the upshift absolute threshold $W_{D,u}$, switching to the fast control takes place in step 261 immediately, the fast control continuing then with step 170 (FIG. 2). There is no additional time threshold for upshifting. Hence, if the rotational speed n of the motor M suddenly decreases due to an additional load, the fast control is enabled for quick compensation.

The electrical hair and skin treating device 300 is schematically illustrated in FIG. 4. The power source 2 (a rechargeable battery), the dc motor M and the drive control 1 are arranged in a main housing 301 of the treating device 300. The motor M drives a drive mechanism 302 arranged at an upper end of the main housing 1. A shaver 303 is releasably coupled to the drive mechanism 302 such that the motor M can drive the shaver 303 via the drive mechanism 302. The shaver 303 is a modular element and can be detached from and reattached to the drive mechanism 302. However, other modular elements (not shown) are provided which can be releasably attached to the drive mechanism 302 and then can be driven by the motor M.

The other elements are a brush, a beard trimmer and a body groomer. For every modular element, a specific target value $U_{emf,0}$ of the induced voltage $U_{emf}$ is provided. Therefore, the closed loop control is adapted to the specific modular element, for example the shaver 303, which is attached to the drive mechanism 302 in FIG. 4.

Summing up, the fast control provides a correction to the control deviation D considerably faster than the slow control. Even quick and large changes of a mechanical load of the motor M can be compensated for by the fast control. In contrast, the slow control prevents annoying fluctuations of the rotational speed n of the motor M when no load or a constant load is applied to the motor M. In both cases, the drive control 1 controls the motor M to run with the desired rotational speed $n_0$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A drive control for driving a dc motor of an electrical household appliance, in particular a hair cutting device such as an electric razor, shaver or epilator, at constant rotational speed, the drive control comprising:

a detection means for determining a parameter indicative of the actual rotational speed of the dc motor, a closed loop control for adjusting a supply voltage ($U_m$) to the dc motor based on a control deviation between a target value and the actual value of the parameter indicative of the rotational speed of the dc motor, wherein the closed loop control has a fast control and a slow control for adjusting the supply voltage with the fast control providing a faster correction of the control deviation than the slow control, and a processor means for determining a switching criterion for switching between the fast control and the slow control, wherein at least one first switching criterion from the slow control to the fast control and at least one second switching criterion, different from the at least one first switching criterion, from the fast control to the slow control are provided, and wherein the close loop control is adapted for switching from the fast control to the slow control, and from the slow control to the fast control, based on the first and second switching criteria.

2. The drive control according to claim 1, wherein at least one of the at least one first switching criterion or the at least one second switching criterion is derived from the parameter indicative of the actual rotational speed.

3. The drive control according to claim 1, wherein at least one of the at least one first switching criterion or the at least one second switching criterion comprises a threshold value for the control deviation.

4. The drive control according to claim 1, wherein the fast control is able to deliver a larger impact on the rotational speed of the dc motor per time unit than the slow control.

5. The drive control according to claim 1, wherein a control output of the fast control has a term proportional, integrative and derivative to the control deviation.

6. The drive control according to claim 1, wherein the change rate of the rotational speed per time unit that can be caused by the slow control is limited by a predetermined maximum change rate.

7. The drive control according to claim 6, wherein the control output of the slow control provides discrete limited steps.

8. The drive control according to claim 1, wherein a slow loop frequency of the slow control is less than a fast loop frequency of the fast control.

9. The drive control according to claim 1, wherein the closed loop control comprises a pulse width modulation module for adjusting the supply voltage ($U_m$) to the dc motor.

10. The drive control according to claim 1, wherein the parameter indicative of the actual rotational speed of the dc motor is the induced motor voltage ($U_{em}$)and the rotational speed defined as rotations per time.

11. The drive control according to claim 10, wherein the detection means for determining a parameter indicative of the actual rotational speed of the dc motor comprises means for determining the dc voltage of the power source of the electrical appliance and means for determining the motor current.

12. An electric hair treating device having a main body with a dc-motor for driving a treating tool, a power source and a drive control according to claim 1.

13. The electric hair treating device according to claim 12, wherein the treating tool is a modular element detachable and re-attachable to the electric hair and skin treating device by coupling the treating tool to a drive mechanism of the electrical hair and skin treating device driven by the dc-motor.

14. The electric hair treating device according to claim 13, wherein the modular element comprises a brush, beard trimmer, a body groomer and/or a shaver.

15. The electric hair treating device according to claim 12, wherein the drive control is adapted to control the rotational speed irrespective of the load to an adjustable target rotational speed.

16. The drive control according to claim 1, wherein:

the at least one first switching criterion comprises the control deviation being greater than a first threshold value, and the at least one second switching criterion comprises the control deviation being less than a second threshold value that is different than the first threshold value.

* * * * *